United States Patent [19]
Akehurst et al.

[11] Patent Number: 5,922,306
[45] Date of Patent: *Jul. 13, 1999

[54] AEROSOL FORMULATIONS CONTAINING P134A AND PARTICULATE MEDICAMENT

[75] Inventors: Rachel Ann Akehurst; Anthony James Taylor; David Andrew Wyatt, all of Ware, United Kingdom

[73] Assignee: Glaxo Group Limited, Greenford, United Kingdom

[*] Notice: This patent is subject to a terminal disclaimer.

[21] Appl. No.: 09/060,110

[22] Filed: Apr. 15, 1998

Related U.S. Application Data

[63] Continuation of application No. 08/462,558, Jun. 5, 1995., Pat. No. 5,744,123, which is a continuation of application No. 08/302,435, Sep. 9, 1994., abandoned, which is a continuation of application No. 08/094,175, Aug. 5, 1993., abandoned

[30] Foreign Application Priority Data

Dec. 12, 1991 [GB] United Kingdom .................. 9126405
Feb. 6, 1992 [GB] United Kingdom .................. 9202522

[51] Int. Cl.⁶ ...................................................... A61K 9/12
[52] U.S. Cl. ............................. 424/45; 424/46; 514/937; 514/826
[58] Field of Search ................ 424/45, 46; 514/937, 514/826

[56] References Cited

U.S. PATENT DOCUMENTS

| | | | |
|---|---|---|---|
| 2,868,691 | 1/1959 | Porush et al. | 167/54 |
| 2,885,427 | 5/1959 | Rob et al. | 260/653.7 |
| 3,014,844 | 12/1961 | Thiel et al. | 167/82 |
| 3,219,533 | 11/1965 | Mullins | 167/82 |
| 3,320,125 | 5/1967 | Grim | 167/54 |
| 3,809,294 | 5/1974 | Torgeson | 222/182 |
| 3,897,779 | 8/1975 | Hansen | 128/266 |
| 4,174,295 | 11/1979 | Bargigia et al. | 252/305 |
| 4,405,598 | 9/1983 | Brown | 424/45 |
| 5,653,962 | 8/1997 | Akehurst et al. | 424/45 |
| 5,674,471 | 10/1997 | Akehurst et al. | 424/45 |

FOREIGN PATENT DOCUMENTS

| | | |
|---|---|---|
| 0 504 112 | 9/1992 | European Pat. Off. . |
| 27 03 119 | 10/1990 | Germany . |
| 90/07333 | 7/1990 | WIPO . |

OTHER PUBLICATIONS

Oberholz, *Frankfurter Allegmeine Zeitung*, Oct. 1989, vol. 25, No. 207, p. 7.

Dalby et al., *Pharmaceutical Technology*, Mar. 1990, vol. 14, No. 3, pp. 26–33.

Amzacort™ carton, William H. Rorer, Inc., Fort Washington, Pennsylvania, USA 19034, 1986.

*Pharmaceutical Journal*, Sep. 29, 1990, vol. 245, pp. 428–429,.

*The Theory and Practice of Industrial Pharmacy*, 2nd Ed., 1976 (Philadelphia, PA: Lea and Febiger), pp. 270 and 276–278.

*Handbook of Aerosol Technology*, 2nd Edition, 1979 (New York, New York: Van Nostrand Reinhold Company), pp. 30, 32, 33, 166, 167, 232, 233.

U.S. Senate Hearings, May 12–14, 1987, 343–347, 437 (U.S. Government Printing Office, Washington, D.C., 1987), CIS:1987–S321–26.

*Hagers Handbook of Pharmaceutical Practice*, 1971, pp. 342–354 (Berlin: Springer–Verlag).

*Primary Examiner*—Raj Bawa
*Attorney, Agent, or Firm*—Bacon & Thomas PLLC

[57] ABSTRACT

A pharmaceutical formulation comprising (i) one or more particulate medicaments, and (ii) 1,1,1,2-tetrafluoroethane as propellant, which formulation contains less than 0.0001% w/w surfactant based upon the weight of medicament, particulate medicament being present in an amount from 0.005 to 5% w/w relative to the total weight of the formulation and having a particle size of less than 100 microns, with the proviso that said medicament is other than salmeterol, salbutamol, fluticasone propionate, beclomethasone dipropionate or a physiologically acceptable salt or solvate thereof and with the proviso that when said formulation consists of betamethasone, ergotamine tartrate or sodium cromoglycate and 1,1,1,2-tetrafluoroethane the weight to weight ratio of medicament to propellant is other than 69:7900 or 0.866% w/w.

34 Claims, No Drawings

AEROSOL FORMULATIONS CONTAINING P134A AND PARTICULATE MEDICAMENT

CROSS REFERENCE TO RELATED APPLICATIONS

This application is a continuation of application Ser. No. 08/462,558, filed Jun. 5,1995 now U.S. Pat. No. 5,744,123 issued on Apr. 28,1998; which is a continuation of application Ser. No. 08/302,435, filed Sep. 9,1994, now abandoned, which is a continuation of application Ser. No. 08/094,175, filed Aug. 5, 1993, now abandoned, which is a 371 application of PCT/EP92/028109.

BACKGROUND OF THE INVENTION

1. Field of the Invention

This invention relates to aerosol formulations of use for the administration of medicaments by inhalation.

The use of aerosols to administer medicaments has been known for several decades. Such aerosols generally comprise the medicament, one or more chlorofluorocarbon propellants and either a surfactant or a solvent, such as ethanol. The most commonly used aerosol propellants for medicaments have been propellant 11 ($CCl_3F$) and/or propellant 114 ($CF_2ClCF_2Cl$) with propellant 12 ($CCl_2F_2$). However these propellants are now believed to provoke the degradation of stratospheric ozone and there is thus a need to provide aerosol formulations for medicaments which employ so called "ozone-friendly" propellants.

A class of propellants which are believed to have minimal ozone-depleting effects in comparison to conventional chlorofluorocarbons comprise fluorocarbons and hydrogen-containing chlorofluorocarbons, and a number of medicinal aerosol formulations using such propellant systems are disclosed in, for example. EP 0372777, WO91/04011, WO91/11173, WO91/11495 and WO91/14422. These applications are all concerned with the preparation of pressurised aerosols for the administration of medicaments and seek to overcome the problems associated with the use of the new class of propellants, in particular the problems of stability associated with the pharmaceutical formulations prepared. The applications all propose the addition of one or more of adjuvants such as alcohols, alkanes, dimethyl ether, surfactants (including fluorinated and non-fluorinated surfactants, carboxylic acids, polyethoxylates etc) and even conventional chlorofluorocarbon propellants in small amounts intended to minimize potential ozone damage.

2. Description of the Prior Art

Thus, for example EP 0372777 requires the use of 1,1,1,2-tetrafluoroethane in combination with both a cosolvent having greater polarity than 1,1,1,2-tetrafluoroethane (e.g. an alcohol or a lower alkane) and a surfactant in order to achieve a stable formulation of a medicament powder. In particular it is noted in the specification at page 3, line 7 that "it has been found that the use of propellant 134a (1,1,1,2-tetrafluoroethane) and drug as a binary mixture or in combination with a conventional surfactant such as sorbitan trioleate does not provide formulations having suitable properties for use with pressurised inhalers". Surfactants are generally recognized by those skilled in the art to be essential components of aerosol formulations, required not only to reduce aggregation of the medicament but also to lubricate the valve employed, thereby ensuring consistent reproducibility of valve actuation and accuracy of dose dispensed. Whilst WO91/11173, WO91/11495 and WO91/14422 are concerned with formulations comprising an admixture of drug and surfactant, WO91/04011 discloses medicinal aerosol formulations in which the particulate medicaments are pre-coated with surfactant prior to dispersal in 1,1,1,2-tetrafluoroethane.

A SUMMARY OF THE INVENTION

We have now surprisingly found that, in contradistinction to these teachings, it is in fact possible to obtain satisfactory dispersions of medicaments in fluorocarbon or hydrogen-containing chlorofluorocarbon propellants such as 1,1,1,2-tetrafluoroethane without recourse to the use of any surfactant or cosolvent in the composition, or the necessity to pre-treat the medicament prior to dispersal in the propellant.

There is thus provided in one aspect of the invention a pharmaceutical aerosol formulation which comprises particulate medicament and a fluorocarbon or hydrogen-containing chlorofluorocarbon propellant, which formulation is substantially free of surfactant and with the proviso that said medicament is other than salmeterol, salbutamol, fluticasone propionate, beclomethasone dipropionate or a physiologically acceptable salt or solvate thereof By "substantially free of surfactant" is meant formulations which contain no significant amounts of surfactant, for example less than 0.0001% by weight of the medicament.

The particle size of the particulate (e.g. micronized) medicament should be such as to permit inhalation of substantially all of the medicament into the lungs upon administration of the aerosol formulation and will thus be less than 100 microns, desirably less than 20 microns, and preferably in the range 1–10 microns, e.g. 1–5 microns.

Medicaments which may be administered in aerosol formulations according to the invention include any drug useful in inhalation therapy which may be presented in a form which is substantially completely insoluble in the selected propellant. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines and pentamidine; antihistamines, e.g. methapyrilene; anti-inflammatories, e.g. flunisolide budesonide, tipredane or triamcinolone acetonide; antitussives, e.g. noscapine; bronchodilators, e.g. ephedrine, adrenaline, fenoterol, fomioterol, isoprenaline, metaproterenol, phenylephrine, phenylpropanolamine, pirbuterol, reproterol, rirniterol, terbutaline, isoetharine, tulobuterol, orciprenaline, or (−)-4-amino-3,5-dichloro-α-[[[6-[2-(2-pyridinyl)-ethoxy]hexyl]amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophyllie, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament and/or to minimize the solubility of the medicament in the propellant.

Particularly preferred medicaments for administration using aerosol formulations in accordance with the invention include anti-allergics, bronchodilators and anti-inflammatory steroids of use in the treatment of respiratory disorders such as asthma by inhalation therapy, for example cromoglycate (e.g. the sodium salt), terbutaline (e.g. the sulphate salt), reproterol (e.g. the hydrochloride salt) or (−)-4-amino-3,5-dichloro-α-[[[6-[2-(2-pyridinyl)-ethoxy]hexyl]amino]methyl]benzenemethanol.

It will be appreciated by those skilled in the art that the aerosol formulations according to the invention may, if desired, contain a combination of two or more active ingredients. Aerosol compositions containing two active ingredients (in a conventional propellant system) are known, for example, for the treatment of respiratory disorders such as asthma. Accordingly the present invention further provides aerosol formulations in accordance with the invention which contain two or more particulate medicaments. Medicaments may be selected from suitable combinations of the medicaments mentioned hereinbefore. Thus, suitable combinations of bronchodilatory agents include ephedrine and theophylline, fenoterol and ipratropium, and isoetharine and phenylephrine aerosol formulations.

Preferred aerosol formulations in accordance with the invention comprise (a) an effective amount of a particulate bronchodilatory medicament (b) an effective amount of a particulate antiinflammatory, preferably a steroidal antiinflammatory medicament and (c) a fluorocarbon or hydrogen-containing chlorofluorocarbon propellant with the proviso that said medicaments are other than salmeterol, salbutamol, fluticasone propionate, beclomethasone dipropionate or a physiologically acceptable salt or solvate thereof. Alternatively aerosol formulations may contain a bronchodilator such as isoprenaline in combination with an antiallergic such as cromoglycate (e.g. the sodium salt). Combinations of isoprenaline and sodium cromoglycate are especially preferred.

The final aerosol formulation desirably contains 0.005–10% w/w, preferably 0.005–5% w/w, especially 0.01–1.0% w/w, of medicament relative to the total weight of the formulation.

The propellants for use in the invention may be any fluorocarbon or hydrogen-containing chlorofluorocarbon or mixtures thereof having a sufficient vapor pressure to render them effective as propellants. Preferably the propellant will be a non-solvent for the medicament. Suitable propellants include, for example, $C_{1-4}$ hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$, $C_{1-4}$ hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$.

Where mixtures of the fluorocarbons or hydrogen-containing chlorofluorocarbons are employed they may be mixtures of the above identified compounds or mixtures, preferably binary mixtures, with other fluorocarbons or hydrogen-containing chlorofluorocarbons for example $CHClF_2$, $CH_2F_2$ and $CF_3CH_3$. Preferably a single fluorocarbon or hydrogen-containing chlorofluorocarbon is employed as the propellant. Particularly preferred as propellants are $C_{1-4}$ hydrogen-containing fluorocarbons such as 1,1,1,2-tetrafluoroethane ($CF_3CH_2F$) and 1,1,1,2,3,3,3-heptafluoro-n-propane ($CF_3CHFCF_3$).

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$.

The propellant may additionally contain a volatile adjuvant such as a saturated hydrocarbon for example propane, n-butane, isobutane, pentane and isopentane or a dialkyl ether for example dimethyl ether. In general, up to 50% w/w of the propellant may comprise a volatile hydrocarbon, for example 1 to 30% w/w. However, formulations which are substantially free of volatile adjuvants are preferred.

It is further desirable that the formulations of the invention are substantially free of liquid components of higher polarity than the propellant employed. Polarity may be determined for example, by the method described in European Patent Application Publication No. 0327777. In particular formulations which are substantially free of alcohols such as ethanol are preferable. As used herein "substantially free" means less than 1% w/w based upon the fluorocarbon or hydrogen-containing chlorofluorocarbons in particular less than 0.5% for example 0.1% or less.

A particularly preferred embodiment the invention provides a pharmaceutical aerosol formulation consisting essentially of one more particulate medicament and one or more fluorocarbon or hydrogen-containing chlorofluorocarbon propellant, with the proviso that said medicament is other than salmeterol, salbutamol, fluticasone propionate, beclomethasone dipropionate or a physiologically acceptable salt or solvate thereof.

The formulations of the invention may be prepared by dispersal of the medicament in the selected propellant in an appropriate container, e.g. with the aid of sonication. The process is desirably carried out under anhydrous conditons to obviate any adverse effects of moisture on suspension stability.

The formulations according to the invention form weakly flocculated suspensions on standing but, surprisingly, these suspensions have been found to be easily redispersed by mild agitation to provide suspensions with excellent delivery characteristics suitable for use in pressurised inhalers, even after prolonged storage. Minimizing and preferably avoiding the use of formulation excipients e.g. surfactants, cosolvents etc in the aerosol formulations according to the invention is also advantageous since the formulations may be substantially taste and odor free, less irritant and less toxic than conventional formulations.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The particle size distribution of the aerosol formulations according to the invention is particularly impressive and may be measured by conventional techniques, for example by cascade impaction or by the "Twin Impinger" analytical process. As used herein reference to the "Twin Impinger" assay means "Determination of the deposition of the emitted dose in pressurised inhalations using apparatus A" as defined in British Pharmacopaeia 1988, pages A204–207, Appendix XVII C. Such techniques enable the "respirable fraction" of the aerosol formulations to be calculated. As used herein reference to "respirable fraction" means the amount of active ingredient collected in the lower impingement chamber per actuation expressed as a percentage of the total amount of active ingredient delivered per actuation using the twin impinger method described above. The formulations according to the invention have been found to have a respirable fraction of 20% or more by weight of the medicament, preferably 25 to 70%, for example 30 to 60%.

Optionally, the medicament may be surface-modified prior to its dispersion in the propellant by treatment with a substantially non-polar liquid medium which is a non-solvent for the medicament. There is thus provided in a further aspect of the invention an aerosol formulation comprising particulate, surface-modified medicament, as defined herein, and a fluorocarbon or hydrogen-containing chlorofluorocarbon propellant, which formulation is substantially free of surfactant. By "surface-modified medicament" is meant particles of medicament which have been surface-modified by admixture with a substantially non-polar non-solvent liquid, followed by removal of the liquid, with the proviso that said medicament is other than salmeterol, salbutamol, fluticasone propionate, beclomethasone dipropionate or a physiologically acceptable salt or solvate thereof. The substantially non-polar non-solvent liquid medium is conveniently an aliphatic hydrocarbon, e.g. a lower alkane, which is sufficiently volatile to permit its ready evaporation, e.g. at ambient temperature and pressure, after slurrying with the medicament. The use of isopentane as liquid medium is particularly advantageous in this respect.

The medicament is desirably slurried with- the liquid medium under anhydrous conditions to obviate any adverse effects of moisture on suspension stability. The slurry may advantageously be sonicated to maximize the surface-modifying effect of the treatment. The liquid may be removed by any convenient means for example by evaporation or by filtration followed by evaporation, provided that following treatment the medicament is substantially free of the liquid. The formulations of the invention will be substantially free of the non-solvent non-polar liquid. Surface-modified medicament prepared by the above described process comprises a further aspect of the present invention.

The formulations according to the invention may be filled into canisters suitable for delivering pharmaceutical aerosol formulations. Canisters generally comprise a container capable of withstanding the vapor pressure of the propellant used such as a plastic or plastic-coated glass bottle or preferably a metal can, for example an aluminium can which may optionally be anodised, lacquer-coated and/or plastic-coated, which container is closed with a metering valve. The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Suitable valves are commercially available from manufacturers well known in the aerosol industry. for example, from Valois, France (e.g. DF10, DF30, DF60), Bespak plc, UK (e.g. BK300, BK356) and 3M-Neotechnic Ltd, UK (e.g. Spraymiser™).

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The particulate medicament is added to a charge vessel and liquified propellant is pressure filled through the charge vessel into a manufacturing vessel. The drug suspension is mixed before recirculation to a filling machine and an aliquot of the drug suspension is then filled through the metering valve into the canister. Typically, in batches prepared for pharmaceutical use, each filled canister is check-weighed, coded with a batch number and packed into a tray for storage before release testing.

Each filled canister is conveniently fitted into a suitable channelling device prior to use to form a metered dose inhaler for administration of the medicament into the lungs or nasal cavity of a patient. Suitable channelling devices comprise for example a valve actuator and a cylindrical or cone-like passage through which medicament may be delivered from the filled canister via the metering valve to the nose or mouth of a patient e.g. a mouthpiece actuator. Metered dose inhalers are designed to deliver a fixed unit dosage of medicament per actuation or "puff", for example in the range of 10 to 5000 microgram medicament per puff.

Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1, 2, 3 or 4 puffs each time.

Thus, for example, each valve actuation may deliver 5 mg sodium cromoglycate, 250 microgram terbutaline sulphate or 500 microgram reproterol hydrochloride. Typically each filled canister for use in a metered dose inhaler contains 100, 160 or 240 metered doses or puffs of medicament.

The filled canisters and metered dose inhalers described herein comprise further aspects of the present invention.

A still further aspect of the present invention comprises a method of treating respiratory disorders such as, for example, asthma, which comprises administration by inhalation of an effective amount of a formulation as herein described.

The following non-limitative Examples serve to illustrate the invention.

EXAMPLE 1

Micronized sodium cromoglycate (1.2 g) is weighed directly into an aluminium can and 1,1,1,2-tetrafluorethane (to 18.2 g) added from a vacuum flask. A metering valve is crimped into place and the sealed can sonicated for five minutes. The aerosol delivers 5 mg sodium cromoglycate per actuation.

EXAMPLE 2

Micronized terbutaline sulphate (60 mg) is weighed directly into an aluminium can and 1,1,1,2-tetrafluorethane (to 18.2 g) added from a vacuum flask. A metering valve is crimped into place and the sealed can sonicated for five minutes. The aerosol delivers 250 microgram terbutaline sulphate per actuation.

EXAMPLE 3

Micronized reproterol hydrochloride (120 mg) is weighed directly into an aluminium can and 1,1,1,2-tetrafluorethane (to 18.2 g) added from a vacuum flask. A metering valve is crimped into place and the sealed can sonicated for five minutes. The aerosol delivers 500 microgram reproterol hydrochloride per actuation.

EXAMPLE 4

Micronized terbutaline sulphate (60 mg) is weighed directly into an aluminium can and 1,1,1,2,3,3,3-heptafluoro-n-propane (to 21.4 g) added from a vacuum flask. A metering valve is crimped into place and the sealed can sonicated for five minutes. The aerosol delivers 250 microgram terbutaline sulphate per actuation.

We claim:

1. A pharmaceutical formulation consisting essentially of (i) one or more particulate medicaments, and (ii) 1,1,1,2-tetrafluoroethane as propellant, which formulation contains less than 0.0001% w/w surfactant based upon the weight of medicament, particulate medicament being present in an amount from 0.005 to 5% w/w relative to the total weight of the formulation and having a particle size of less than 100 microns, with the proviso that said medicament is other than salmeterol, salbutamol, fluticasone propionate, beclomethasone dipropionate or a physiologically acceptable salt or solvate thereof and with the proviso that when said formulation consists of betamethasone, ergotamine tartrate or sodium cromoglycate and 1,1,1,2-tetrafluoroethane the weight to weight ratio of medicament to propellant is other than 69:7900 or 0.866% w/w.

2. A formulation as claimed in claim 1 which is free of surfactant.

3. A formulation as claimed in claim 1 wherein said medicament is an anti-allergic, a bronchodilator or an anti-inflammatory steroid.

4. A formulation as claimed in claim 1 wherein said medicament is a bronchodilator.

5. A formulation as claimed in claim 1 wherein said medicament is pirbuterol or a physiologically acceptable salt thereof.

6. A formulation as claimed in claim 1 which contains two or more particulate medicaments.

7. A formulation as claimed in claim 1 which comprises a particulate bronchodilatory medicament and a particulate anti-inflammatory medicament.

8. A formulation as claimed in claim 1 which comprises a particulate bronchodilatory medicament and a particulate anti-allergic medicament.

9. A formulation as claimed in claim 1 which comprises isoprenaline and cromoglycate or a physiologically acceptable salt thereof.

10. A formulation as claimed in claim 1 which contains 0.01 to 1% w/w of medicament relative to the total weight of the formulation.

11. A formulation as claimed in claim 1 which has a respirable fraction of 20% or more by weight of medicament.

12. A formulation as claimed in claim 1 wherein said medicament is an anti-allergic medicament selected from the group consisting of ketotifen, nedocromil and physiologically acceptable salts thereof.

13. A formulation as claimed in claim 1 wherein said medicament is an anti-inflammatory medicament selected from the group consisting of budesonide and triamcinolone acetonide.

14. A formulation as claimed in claim 1 wherein said medicament is an anti-inflammatory medicament which is flunisolide.

15. A formulation as claimed in claim 1 wherein said medicament is an anti-cholinergic medicament selected from the group consisting of ipratropium, atropine, oxitropium and physiologically acceptable salts thereof.

16. A formulation as claimed in claim 1 wherein said medicament is a xanthine selected from the group consisting of aminophylline, choline theophyllinate, lysine theophyllinate, theophylline and physiologically acceptable salts thereof.

17. A formulation as claimed in claim 1 wherein said medicament is cromoglycate or a physiologically acceptable salt thereof.

18. A pharmaceutical aerosol formulation consisting of (i) one or more particulate medicaments, and (ii) 1,1,1,2-tetrafluoroethane as propellant, particulate medicament being present in an amount from 0.005 to 5% w/w relative to the total weight of the formulation and having a particle size of less than 100 microns, with the proviso that said medicament is other than salmeterol, salbutamol, fluticasone propionate, beclomethasone dipropionate or a physiologically acceptable salt or solvate thereof and with the proviso that when said formulation consists of betamethasone, ergotamine tartrate or sodium cromoglycate and 1,1,1,2-tetrafluoroethane the weight to weight ratio of medicament to propellant is other than 69:7900 or 0.866% w/w.

19. A formulation as claimed in claim 1 wherein said medicament is an anti-allergic, a bronchodilator or an anti-inflammatory steroid.

20. A formulation as claimed in claim 1 wherein said medicament is a bronchodilator.

21. A formulation as claimed in claim 1 wherein said medicament is pirbuterol or a physiologically acceptable salt thereof.

22. A formulation as claimed in claim 1 which contains two or more particulate medicaments.

23. A formulation as claimed in claim 1 which comprises a particulate bronchodilatory medicament and a particulate anti-inflammatory medicament.

24. A formulation as claimed in claim 1 which comprises a particulate bronchodilatory medicament and a particulate anti-allergic medicament.

25. A formulation as claimed in claim 1 which comprises isoprenaline and cromoglycate or a physiologically acceptable salt thereof.

26. A formulation as claimed in claim 1 which contains 0.01 to 1% w/w of medicament relative to the total weight of the formulation.

27. A formulation as claimed in claim 1 which has a respirable fraction of 20% or more by weight of medicament.

28. A formulation as claimed in claim 1 wherein said medicament is an anti-allergic medicament selected from the group consisting of ketotifen, nedocromil and physiologically acceptable salts thereof.

29. A formulation as claimed in claim 1 wherein said medicament is an anti-inflammatory medicament selected from the group consisting of budesonide and triamcinolone acetonide.

30. A formulation as claimed in claim 1 wherein said medicament is an anti-inflammatory medicament which is flunisolide.

31. A formulation as claimed in claim 1 wherein said medicament is an anti-cholinergic medicament selected from the group consisting of ipratropium, atropine, oxitropium and physiologically acceptable salts thereof.

32. A formulation as claimed in claim 18 wherein said medicament is a xanthine selected from the group consisting of aminophylline, choline theophyllinate, lysine theophyllinate, theophylline and physiologically acceptable salts thereof.

33. A pharmaceutical aerosol formulation consisting essentially of (i) one or more particulate medicaments, and (ii) 1,1,1,2-tetrafluoroethane as propellant, which formulation is free of surfactant, particulate medicament being present in an amount from 0.005 to 5% w/w relative to the total weight of the formulation and having a particle size of less than 100 microns, with the proviso that said medicament is other than salmeterol, salbutamol, fluticasone propionate, beclomethasone dipropionate or a physiologically acceptable salt or solvate thereof and which formulation contains less than 0.866% w/w of medicament relative to the total weight of the formulation.

34. A pharmaceutical aerosol formulation consisting essentially of (i) one or more particulate medicaments, and (ii) 1,1,1,2-tetrafluoroethane as propellant, which formulation is free of surfactant, particulate medicament being present in an amount from 0.005 to 5% w/w relative to the total weight of the formulation and having a particle size of less than 100 microns, with the proviso that said medicament is other than salmeterol, salbutamol, fluticasone propionate, beclomethasone dipropionate or a physiologically acceptable salt of solvate thereof and which formulation contains 0.005 to 0.659% w/w medicament relative to the total weight of the formulation.

* * * * *